United States Patent [19]

Anderson et al.

[11] Patent Number: 4,536,179
[45] Date of Patent: Aug. 20, 1985

[54] IMPLANTABLE CATHETERS WITH NON-ADHERENT CONTACTING POLYMER SURFACES

[75] Inventors: Michael H. Anderson; Christopher S. Lyons, both of St. Paul; Bruce D. Wigness, Minneapolis, all of Minn.

[73] Assignee: University of Minnesota, Minneapolis, Minn.

[21] Appl. No.: 422,758

[22] Filed: Sep. 24, 1982

[51] Int. Cl.³ .............................................. A61M 25/00
[52] U.S. Cl. .................... 604/266; 604/280; 128/DIG. 14; 128/DIG. 21; 427/2; 427/39
[58] Field of Search .................. 128/1 R, 348.1, 772, 128/DIG. 14, DIG. 21; 523/105, 112; 604/93, 264, 265, 266, 175, 272–274, 280; 3/1, 1.4; 427/2, 39, 228, 41

[56] References Cited

U.S. PATENT DOCUMENTS

| | | | |
|---|---|---|---|
| 2,814,296 | 11/1957 | Everett | 604/272 |
| 3,703,585 | 11/1972 | Agnone et al. | |
| 3,922,378 | 11/1975 | Kline | 128/772 |
| 4,100,113 | 7/1978 | McCain | |
| 4,125,152 | 11/1978 | Kestner et al. | |
| 4,160,454 | 7/1979 | Foux | 604/175 |

OTHER PUBLICATIONS

Chem. Abst.; vol. 95; 1981; No. 95: 209403q; "Thin Film Dep. by Plasma Poly. and Its App."; Hozumi et al.; Jitsumu Hyomen Gijutsu; 1981, 28(7); pp. 318–323 (Japanese).

"Silastic Intravenous Catheter"; Stewart et al.; The Bulletin of the Dow Corning Cent. for Aid to Med. Res.; Apr. 1962; pp. 5–6.

K. G. Budinski, J. Vac. Sci. Technol., 12:786–789, 1975.

Primary Examiner—Richard J. Apley
Assistant Examiner—Gregory Beaucage
Attorney, Agent, or Firm—Burd, Bartz & Gutenkauf

[57] ABSTRACT

Catheters for long term implantation having polymer surfaces in face-to-face contact which are provided with a thin film coating of a glow discharge plasma polymerized fluorocarbon to prevent adhesion of the contacting surfaces. The polymerized fluorocarbon film, between about 50 and 1000 Angstroms in thickness, is bonded to the substrate material giving a low surface energy without changing its bulk properties. The low surface energy will prevent adhesion of cured polymer surfaces in contact and act as a lubricant. The smooth pinhole-free films will control or prevent diffusion into or out of the bulk material. These biocompatible films provide an alternative use for polymers whose bulk properties are unacceptable but whose surface properties are desirable.

8 Claims, No Drawings

IMPLANTABLE CATHETERS WITH NON-ADHERENT CONTACTING POLYMER SURFACES

BACKGROUND OF THE INVENTION

1. Field of the Invention

This invention is directed to catheters adapted for long term implantation within living bodies and characterized by non-adherent contacting polymer surfaces. In some catheter designs, polymer films are in close contact with polymer surfaces. Two catheters of this type are disclosed in the copending Dorman application Ser. No. 245,379, filed Mar. 19, 1981, and the copending Wigness et al application Ser. No. 367,683, filed Apr. 12, 1982, hereafter referred to as the check valve catheter and the vascular access catheter, respectively. Both applications are of common ownership with the present application.

The preferred form of the check valve catheter consists of a thin silicone rubber sleeve stretched over a silicone rubber catheter. Silicone rubber surfaces in contact will adhere over time. This can result from the attraction of some compounds to chemically similar compounds and a knitting phenomenon where loose polymer chains at the surface become woven together. This adhesion greatly compromises the long term operation of the check valve catheter. During its development, a method of eliminating this adhesion was researched. A method of impregnating the rubber with a lubricant gave a temporary solution, but a permanent solid lubricant that would not leach out was desired. Films of graphite and albumin were sandwiched between the sleeve and the catheter but did not reduce adhesion significantly. Although silicone rubber has a low surface energy which is known to reduce adhesion, its ability to knit into a surface increases the actual surface contact causing a net increase of adhesion. For these reasons, a smooth film of lower surface energy than silicone rubber was desired.

The vascular access catheter consists of a flexible partition inside the catheter that can be shifted to one side to expose an inner lumen, thus enabling blood withdrawal or infusion. In its preferred form, it is made of silicone rubber and over time the contacting surfaces adhere to one another.

A fluorocarbon surface, such as polytetrafluoroethylene (PTFE) is known to have the desired nonadhering qualities. Glow discharge plasma polymerization of fluorocarbons is the only method known to provide the conditions necessary to react fluorine groups with the inert methyl groups on the surface of silicone rubber.

2. The Prior Art

Plasma polymerization of TFE has been widely studied in the last decade. Although most of the studies are aimed at understanding the process, a few specific applications have been cited and patents that include the process have been granted. U.S. Pat. No. 4,125,152, granted on Nov. 14, 1978, discloses the use of plasma polymerization of TFE to prevent adherent scale deposition on heat transfer surfaces in contact with heat transfer fluids. U.S. Pat. No. 4,100,113, granted on July 11, 1978, discloses the use of plasma polymerization of TFE in the preparation of electrolytic cell membranes by polymerization onto polymer substrates.

U.S. Pat. No. 3,703,585, granted on Nov. 21, 1972, discloses a process of sputtering PTFE polymer onto a substrate. This process differs from plasma polymerization of TFE in that a glow discharge using an inert gas such as argon is used to break off free radicals from the base material. The radicals are then able to deposit onto a substrate. This process has been studied for applying lubricant to small parts (K. G. Budinski, J. Vac. Sci. Technol. 12:786–789, 1975).

SUMMARY OF THE INVENTION

Broadly stated, the invention is directed to catheters for long term implantation within living bodies which are composed of flexible inert non-toxic biocompatible polymeric material and which have surfaces in close face-to-face contact. The catheters are characterized by a thin film glow discharge plasma polymerized fluorocarbon coating on at least one of the contacting surfaces. The ultra-thin coating having a thickness in the range between about 50 and 1000 Angstroms prevents adhesion of cured polymer surfaces in contact and acts as a lubricant. The films are smooth and pinhole-free so as to control or prevent diffusion into or out of the polymer substrate. The films are biocompatible and do not change the bulk properties of the substrate materials.

DETAILED DESCRIPTION OF THE PREFERRED EMBODIMENT

Methods of producing plasma polymerized coatings on surfaces from fluorocarbon monomers are widely known in the art. In carrying out the present invention, plasma polymerization is achieved by producing an electric glow discharge in a gas at ranges of 30–300 mtorr of pressure. A partially ionized gas or plasma is created when released electrons ionize the gas by inducing chain collisions. Radio frequency of 13.56 Mhz is most often used. However, audio frequency, 60 cycle, D.C., and microwave plasmas may also be used. When polymerization is carried out in the presence of a substrate, polymer is deposited uniformly on the exposed surfaces. While tetrafluoroethylene (TFE) is the preferred monomer, the process is applicable to a variety of other fluorocarbon monomers. These include, but are not limited to, hexafluoropropylene, perfluorobutene-2, chlorotrifluoroethylene, difluoroethylene, and the like.

In its simplest form, a plasma reactor consists of an air-tight chamber with an inlet for monomer and an outlet to a vacuum pump. The chamber is fitted with either capacitor plates or an inductor coil. These may be placed inside or outside of the reactor in such fashion that the fields generated are sufficient to produce glow over a substantial region of the incoming monomer when connected to a frequency generator. Bell-jar and cylindrical flow through reactors are the most common.

Conditions such as pressure, monomer flow rate, power input and position of substrates relative to the glow are variables within the skill of the plasma polymerization art that depend upon the films desired and the reactor design.

For high quality PTFE-like films, TFE monomer is metered into the reaction chamber and into the glow region. The power input into the glow region is set to maintain a deep violet glow. If a bluewhite glow is prevalent, a fluorine-poor polymer may result. The substrate should be placed downstream and out of the glow region. It must be far enough from the glow so that the undesirable high energy species, including electrons, ions, metastables and UV photons, do not interfere with the free radical polymerization of TFE at the surface of the substrate. The flow rate must be adjusted so that the desirable radicals can reach the substrate before terminating in the gas phase or attacking the reactor wall. Finally, the pumping rate should be adjusted to give pressures in the range of 150-250 mtorr. The inventors have found these general conditions to give films very similar to PTFE surfaces produced by other methods, as confirmed by contact angle measurements and Electron Spectroscopy for Chemical Analysis (ESCA).

ESCA is a major tool for surface analysis due to its low penetration of 50 Angstroms or less. In ESCA, binding energy of inner shell electrons is measured which gives information about the elements on the surface. In general, the energy shift of the $C_{1s}$ electron due to functional groups is too small for ESCA to be useful for structural analysis. Fluorine, however, produces energy shifts of about 2 eV per fluorine atom for the $C_{1s}$ electron making ESCA quite useful for distinguishing functional groups containing fluorine.

The ESCA $C_{1s}$ peak is split into series of peaks corresponding to $-CF_3$(294 eV), $-CF_2-CF_2$ (292 eV), $-CF_2-C-$(290 eV), $-CF-C-$(288 eV) and groups of lower energy corresponding to hydrocarbons and carbon bound to $-CF_2$. Shifts to higher energies for the peaks listed occur due to charging effects and must be corrected.

In a pair of experiments one sample was located 2 cm downstream of the glow with 2.3 watts input power and a flow rate of 35 cm$^3$min$^{-1}$. The ESCA scan showed a large response at 292 eV (after adjusting for charging) and moderate responses at 294 eV, 290 eV, and 288 eV. The other sample was located 7.5 cm downstream with 3 watts input power and flow rate of 60 cm$^3$min$^{-1}$ and showed much smaller responses at the latter three positions. The second sample showed high concentration of $-CF_2-CF_2$ indicating polymerization by chain growth giving films similar to PTFE. The first sample showed concentration of $-CF_2-C-$ and $-CF-C-$ indicating fluorine abstraction and polymer cross-linking in the film resulting from the more undesirable, higher energy species. The second sample showed response at 285 eV from methyl groups on the surface of the silicone rubber substrate and indicates a film of less than 50 Angstroms thick. Conditions similar to the second sample provide superior non-adherent films. These scans demonstrate the importance of positioning the samples sufficiently far from the glow.

Contact angles provide information about surface energy and have been found to correlate well with ESCA analysis. The contact angle of a liquid on a solid surface increases as the surface energy decreases. Thus, high contact angles reflect the liquid's inability to spread or wet the surface. Visual contact angles are sufficient to compare the surface energies of the scans of the experimental samples to silicone rubber and PTFE. Films polymerized under the conditions of the second experiment are indistinguishable from PTFE while the conditions of the first experiment give contact angles higher than silicone rubber but less than PTFE. Critical surface tension measurements introduced by W. A. Zisman (Science 162:1360-1368, 1968) give the most reliable index of surface energy. Studies have reported critical surface tensions of 12 and 18 dynes/cm compared to 18 dynes/cm for PTFE under conditions similar to the plasma of the second experiment. (D. F. O'-Kane et al, J. Macromol. Sci-Chem. A10:567-577, 1976, and B. D. Washo, J. Macromol. Sci-Chem. A10:5-59-566, 1976).

The manner in which the plasma polymerization process can be used in assembling the check valve catheter and the vascular access catheter is illustrated by the following.

Construction of the check valve catheter begins with a silicone rubber catheter tube (0.090"OD×0.015"ID) which is cut to the desired length. The end is plugged and exit ports are cut into the side of the tip. The area that the sleeve will cover is treated with a TFE plasma to eliminate adhesion of the sleeve to the catheter. A masking technique must be used to prevent TFE polymerization onto areas where it is not needed.

A sleeve of wall thickness 0.003" is cast around a mandrel 0.083" in diameter from silicone rubber. The sleeve is trimmed to length and mounted onto the treated area of the catheter. The sleeve is glued to the catheter by dipping into a liquid silicone rubber mixture, let cure and trimmed. The squeeze fit between the sleeve and catheter provides a positive opening pressure and forms a uni-directional flow tip. The TFE film has been the most dependable method to date to lubricate the sleeve and allows the catheter to remain only a two piece construction of silicone rubber.

To begin assembly of the vascular access catheter, a silicone rubber tube 0.052"ID×0.062"OD is wrapped spirally around a small cylinder in a manner that flattens the tube and exposes one-half of its circumference. This is then treated with a TFE plasma. Upon removal from the cylinder, the result is a tube with one-half of its circumference over its whole length covered with a PTFE-like film. This is then dipped into a liquid silicone rubber mixture that gives a 0.100" overall catheter diameter when cured. The treated half of the wall easily separates from the dipped coating. After the inside wall is glued down at the tip, application of a vacuum to the inner lumen of the catheter collapses the inner wall forming the active state. In this state, fluid can move through the catheter. The inner wall can then be shifted back thus displacing any fluid in the exposed lumen forming the dormant state. The film also prevents the post-curing adhesion of the silicone rubber surfaces. This manufacturing technique facilitates the construction of this catheter and improves the quality and dependability.

The prior patents, copending applications, and publications cited herein are incorporated by reference to the extent that might be necessary for a full and complete understanding of the present invention.

It is apparent that many modifications and variations of this invention as hereinbefore set forth may be made without departing from the spirit and scope thereof. The specific embodiments described are given by way of example only and the invention is limited only by the terms of the appended claims.

We claim:

1. A catheter for long term implantation within a living body composed of concentric tubular elements of flexible inert non-toxic biocompatible polymeric material and having abutting surfaces between the concentric tubular elements in close face-to-face contact, said catheter characterized by the surface of at least one of said tubular elements having a thin film glow discharge plasma polymerized fluorocarbon coating to prevent adhesion to the contacting surface of the other concentric tubular element.

2. A catheter according to claim 1 wherein said coating is between about 50 and 1000 Angstroms thick.

3. A catheter according to claim 1 wherein said fluorocarbon is selected from the class consisting of tetrafluoroethylene, hexafluoropropylene, perfluorobutene-2, chlorotrifluoroethylene and difluoroethylene.

4. A catheter according to claim 1 wherein said catheter is composed of silicone rubber and said coating is polymerized from tetrafluoroethylene.

5. A method of treating catheters for long term implantation within a living body having concentric tubular elements with polymer surfaces between the tubular elements in face-to-face contact to prevent adhesion of the contacting surfaces, said method comprising applying a thin film glow discharge plasma polymerized biocompatible, fluorocarbon coating to the surface of at least one of said tubular elements prior to assembly of the catheter, and then assembling the catheter.

6. A method according to claim 5 wherein said coating is applied to a thickness of between about 50 to 1000 Angstroms.

7. A method according to claim 5 wherein said fluorocarbon is selected from the class consisting of tetrafluoroethylene, hexafluoropropylene, perfluorobutene-2, chlorotrifluoroethylene and difluoroethylene.

8. A method according to claim 5 wherein said catheter is composed of silicone rubber and said coating is polymerized from tetrafluoroethylene.

* * * * *

UNITED STATES PATENT AND TRADEMARK OFFICE
CERTIFICATE OF CORRECTION

PATENT NO. : 4,536,179
DATED : August 20, 1985
INVENTOR(S) : Michael H. Anderson et al It is certified that error appears in the above-identified patent and that said Letters Patent is hereby corrected as shown below:

Column 3, lines 22 and 23, "$-CF_3$(294 eV), $-CF_2-CF_2$ (292 eV), $-CF_2-C-$(290 eV), $-CF-C-$(288 eV)"

should be:

-- $-\overset{*}{C}F_3$(294 eV), $-\overset{*}{C}F_2-CF_2$ (292 eV), $-\overset{*}{C}F_2-C-$ (290 eV), $-\overset{*}{C}F-C-$ (288 eV) --

Signed and Sealed this

Fifteenth Day of October 1985

[SEAL]

Attest:

Attesting Officer

DONALD J. QUIGG

*Commissioner of Patents and Trademarks—Designate*